United States Patent [19]

Thompson et al.

[11] Patent Number: 4,753,891
[45] Date of Patent: Jun. 28, 1988

[54] SCHIFF TEST FOR RAPID DETECTION OF LOW LEVELS OF ALDEHYDES

[75] Inventors: Ralph P. Thompson; Ray A. Damanczuk, both of Oklahoma City, Okla.

[73] Assignee: Akzo N.V., Velperseg, Netherlands

[21] Appl. No.: 890,994

[22] Filed: Jul. 25, 1986

Related U.S. Application Data

[63] Continuation-in-part of Ser. No. 738,138, May 24, 1985, abandoned.

[51] Int. Cl.$^4$ ............................................. G01N 21/78
[52] U.S. Cl. ..................................... 436/130; 436/128; 436/166
[58] Field of Search ............... 436/100, 102, 119, 122, 436/128, 130, 166

[56] References Cited

U.S. PATENT DOCUMENTS

| | | | |
|---|---|---|---|
| 3,433,597 | 3/1969 | Lyshkow | 436/122 |
| 4,036,589 | 7/1977 | King | 436/130 X |
| 4,201,693 | 5/1980 | Hurt et al. | 436/128 |

FOREIGN PATENT DOCUMENTS 1018878 10/1977 Canada ................................. 436/128

OTHER PUBLICATIONS

Dutt, Indian J. Exp. Boil., vol. 18, pp. 962–964, 1980.
Dutt, Cell. Mol. Biol., vol. 27, pp. 175–179, 1981.
Dutt, Indian J. Exp. Biol., vol. 19, pp. 170–172, 1981.
Kramm et al., Anal. Chem., vol. 27, No. 7, pp. 1076–1079, 1955.
Patai, "The Chemistry of the Carbonyl Group", Interscience Publishers, New York, pp. 381–382, 1966.
Shriner et al., "The Systematic Identification of Organic Compounds", 5th Ed., John Wiley & Sons, Inc., New York, pp. 129–130.
Walker, "Formaldehyde", 3rd Ed., Rinehold Publishing Corporation, New York, pp. 467–469.
Puchtler et al., Histochemistry, vol. 40, pp. 291–299, 1974 and vol. 41, pp. 185–194, 1975.
Horobin et al., Histochemical Journal, vol. 3, pp. 371–378, 1971.
Swinehary, "Organic Chemistry: An Experimental Approach", Prentice-Hall, Inc., pp. 423–434, 1969.

*Primary Examiner*—Barry S. Richman
*Assistant Examiner*—Robert J. Hill, Jr.
*Attorney, Agent, or Firm*—William M. Blackstone

[57] ABSTRACT

An improved Schiff's reagent for detection of aldehydes (such as formaldehyde and gluteraldehyde) contains a para-rosaniline compound (such as para-rosaniline hydrochloride), orthophosphoric acid, a bisulfite compound (such as sodium metabisulfite), a phosphate compound (such as sodium orthophosphate monobasic), and water. This reagent provides lower detection levels and faster results than the reagents of the prior art, and is particularly useful in testing the rinse solutions of reusable medical equipment (such as hemodialysis equipment).

19 Claims, No Drawings

SCHIFF TEST FOR RAPID DETECTION OF LOW LEVELS OF ALDEHYDES

RELATED APPLICATIONS

This application is a continuation-in-part of Ser. No. 738,138, filed 1985 May 24, now abandoned.

BACKGROUND OF THE INVENTION

The chemical reactivity of aldehydes in general, and formaldehyde in particular, provides a wide variety of methods for their detection. However, many of these methods are not specific for formaldehyde, and some are not even specific for aldehydes in general. The use of Schiff's reagent for the detection of small quantities of formaldehyde has been widely used because it is both extremely simple and fairly sensitive. It is based on Denige's discovery that Schiff's fuchsin-bisulfite reagent gives a specific coloration with formaldehyde when employed in the presence of strong acids. A typical formulation for a modern version of Schiff's reagent involves a combination of sulphur dioxide and fuchsin (para-rosaniline hydrochloride). The sulphur dioxide is typically generated by mixing sodium bisulfite (NaHSO$_3$) with hydrochloric acid. A typical formulation is as follows:

Dissolve 0.2 g of pure para-rosaniline hydrochloride in 120 ml of hot water. Cool and dissolve 2 g of anhydrous sodium bisulfite, followed by 2 ml of concentrated hydrochloric acid. Dilute the solution to 200 ml with water and store in well-filled amber bottles. The reagent is ready for use after standing at room temperature for about one hour. To employ the test, add 1 ml of concentrated sulphuric acid to 5 ml of the solution to be tested. Cool to room temperature and add 5 ml of the Schiff's reagent. The presence of formaldehyde is indicated by the development of a blue-violet color after 10 to 15 minutes.

Typical formulations in test procedures are taught by J. S. Swinehart, ORGANIC CHEMISTRY: AN EXPERIMENTAL APPROACH, Prentice-Hall, Inc. (1969), pages 423-424; J. F. Walker, FORMALDEHYDE, Third Edition, Rinehold Publishing Corporation, pages 467-469; S. Patai, THE CHEMISTRY OF THE CARBONYL GROUP, Interscience Publishers (1966), pages 381-382; and R. L. Shriner, THE SYSTEMIC IDENTIFICATION OF ORGANIC COMPOUNDS, John Wiley and Sons, Inc., Fifth Edition, pages 129-130. H. Puchtler, ON THE BINDING OF SCHIFF'S REAGENT AND THE PAS REACTION, *HISTOCHEMISTRY* 40, 291-299 (1974), discusses the Schiff's reaction in studies using molecular models. R. W. Horobin, A MECHANISTIC STUDY OF HISTOCHEMICAL REACTIONS BETWEEN ALDEHYDES AND BASIC FUCHSIN IN ACID ALCOHOL USED AS A SIMPLIFIED SUBSTITUTE FOR SCHIFF'S REAGENT, *HISTOCHEMICAL JOURNAL* 3 (1971) at 371-378, discusses the use of fuchsin in combination with an acid and an alcohol as a substitute for a conventional Schiff's reagent. H. Puchtler, ON THE HISTORY OF BASIC FUCHSIN ON ALDEHYDE-SCHIFF'S REACTIONS FROM 1862 to 1935, *HISTOCHEMISTRY* 41, 185-194 (1975), discusses the history of reactions employing fuchsin.

Despite the extensive use which has been made of Schiff's reagents for detection of formaldehyde, there is a need for improvements. Specifically, even the best Schiff's reagent formulations tend to take a long time for the color change (i.e., from 10 to 15 minutes), and have a fairly high lower level detection limit (i.e., about 10 mg/L for formaldehyde and about 20 mg/L for gluteraldyhyude). In many fields, including hemodialysis, in which the equipment is sterilized with formaldehyde and then must be thoroughly rinsed and checked for the presence of residual formaldehyde, it would be very desirable to have an improved Schiff's reagent test which would indicate the presence of formaldehyde in a shorter time, and at lower concentrations than is presently possible.

SUMMARY OF THE INVENTION

In one aspect, the invention is a method of preparing a modified Schiff's reagent comprising contacting together (a) a para-rosaniline compound, (b) orthophosphoric acid, (c) a bisulfite compound, (d) a phosphate compound, and (e) water. In another aspect, the invention is a modified Schiff's reagent comprising (a) a para-rosaniline compound, (b) orthophosphoric acid, (c) a bisulfite compound, (d) a phosphate compound, and (e) water. In yet another aspect, the invention is a method of detecting an aldehyde in an aqueous solution comprising (i) contacting the solution to be tested with the aforementioned reagent, and (ii) detecting whether a color change occurs.

The Schiff's reagent of the invention allows the rapid and accurate detection of low levels of aldehydes, including formaldehyde and gluteraldehyde. Detection of both formaldehyde and gluteraldehyde can occur at room temperature in less than 10 minutes at concentrations of only 1-2 mg/L.

DETAILED DESCRIPTION OF THE INVENTION

One component of the reagent of the invention is a "para-rosaninine compound", preferably para-rosaniline hydrochloride, otherwise known as fuchsin. This is a well-known compound having the formula:

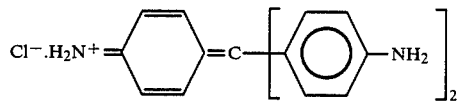

Other suitable para-rosaniline compounds include para-rosaniline acetate, the freebase, and any other related pararosaniline compound which is available. The para-rosaniline compound is generally present in the reagent in a concentration of 0.1 to 0.8 g/L (about 0.3-2.5 millimoles/L), preferably 0.3 to 0.5 g/L (about 0.9-1.5 millimoles/L), and most preferably 0.35 to 0.45 g/L (about 1.1-1.4 millimoles/L).

Another component of the reagent of the invention is a "bisulfite compound" which is an alkali metal or alkaline earth metal metabisulfite or bisulfite. Preferred species are sodium metabisulfite (Na$_2$S$_2$O$_5$) and sodium bisulfite (NaHSO$_3$). Generally, sodium metabisulfite is the chief component of commercial dry sodium bisulfite. Most of the properties and uses of these two compounds are practically identical when dissolved in water according to available sulphur dioxide. The corresponding potassium compounds are also desirable and useful. The bisulfite compound is generally present at a concentration of 1 to 4 g/L (about 5.3-21.0 millimoles/L), preferably 1.5 to 2.5 g/L (about 7.9-13.2 millimoles/L), and most preferably 1.9 to 2.1 g/L (about 10–11 millimoles/L).

Another component of the reagent of the invention is a "phosphate compound" which is an alkali metal or alkaline earth metal orthophosphate monobasic, orthophosphate dibasic or orthophosphate tribasic. Preferred are the sodium compounds, i.e., sodium orthophosphate monobasic (also known as sodium phosphate) ($NaH_2PO_4$), sodium orthophosphate dibasic ($Na_2HPO_4$), and sodium orthophosphate tribasic ($Na_3PO_4$). The corresponding potassium phosphate salts are also desirable and useful. Most of the properties and uses of these compounds are practically identical when dissolved in water on a molar basis according to available phosphate with appropriate adjustments in the amount of phosphoric acid. The phosphate compound is generally present at a concentration of 100 to 400 g/L, preferably 250 to 350 g/L, and most preferably 290 to 310 g/L.

Another component of the reagent of the invention is orthophosphate acid (also known as phosphoric acid) ($H_3PO_4$), which is a well known, commercially available chemical. The orthophosphoric acid is generally present at a concentration of about 30 to 125 g/L, preferably 75 to 110 g/L, and most preferably 90 to 100 g/L, or as required to obtain a pH of 2.1 to 2.9.

An important consideration in preparing the reagent is to maximize the amount of the para-rosaniline compound. Generally, it is convenient to prepare a saturated solution having undissolved para-rosaniline compound, and to then filter off the solid material. Lower amounts will increase the reaction time. The presence of a large amount of para-rosaniline compound is more important for detecting gluteraldehyde than for formaldehyde.

Another item of importance is to have a sufficient quantity of bisulfite compound present to react with the para-rosaniline compound quantitatively to form levoparaosanilinsulfonic acid. However, care must be taken to avoid a large excess of bisulfite compound. If insufficient bisulfite compound is used, false positive results will occur, and excess will cause a decrease in sensitivity. It is generally desirable to have a molar ratio of bisulfite compound to para-rosaniline compound of 20:1–3:1, preferably 15:1–6:1, most preferably about 10:1.

Another important consideration is the pH of the solution. The orthophosphoric acid is used to titrate the pH of the solution to a pH of about 2.1 to 2.9, preferably 2.1 to 2.3, and most preferably 2.15 to 2.25. If the pH is too low, a reduction in sensitivity occurs and if too high, false positive occurs. If the reagent is to be used to detect gluteraldehyde rather than formaldehyde, a pH of 2.65 to 2.75 is preferred. Such a reagent is, however, more susceptible to false positive results from the presence of saline or high pH buffered solutions.

The components of the reagent may be added in any order, but conveniently the phosphate compound is added to water to form a nearly saturated solution. The orthophosphoric acid is then added to bring the pH near the preferred level. It is preferable to allow this buffer solution to age overnight (12–16 hours) to stabilize the pH. The aging is followed by sufficient additional phosphoric acid to form a solution having a pH of about 2.2, preferably ±0.05. Then, the para-rosaniline and bilsulfite compound are added in mixed form. The reagent should be stored in a well-filled, sealed container (plastic or glass).

The reagent may contain other ingredients such as dyes or additional chemicals in amounts that do not cause undue adverse effects on performance. For instance, a minor portion (e.g., 5%) of the phosphoric acid may be substituted with hydrochloric acid with little effect.

The reagent is used by mixing together a small portion of the reagent with a large portion of the solution to be tested. Typically, the reagent to test solution ratio will be from 1:1 to 1:10, preferably from 1:2.5 to 1:5, on a volume basis. For detecting formaldehyde, a ratio of 1:5 is preferred, and for gluteraldehyde, a ratio of 1:2.5 is preferred. The reagent quantitatively detects aldehydes, including formaldehyde, at concentrations as low as 1 mg/L within about 10 minutes at room temperature. Conventional Schiff's reagents are useful only to about 10 mg/L formaldehyde, and do not detect gluteraldehyde at all until its concentration is at least about 20 mg/L.

Although temperature is not critical, warmer temperatures will cause faster results and lower detection limits. Temperatures of 15° C.–45° C. are preferred, and 20° C.–40° C. is more preferred. Test times at 23° C. are at least twice as long as those at 37° C.

The reagent is slightly straw colored, but when diluted in the test solution, will appear clear (water white). The presence of an aldhyde is indicated by a change of color from clear to pink. Although the color change may be detected spectrophotometrically, it may also be visually observed. The reaction with formaldehyde is virtually identical to that with gluteraldehyde.

Although it is possible to use the reagent by merely determining if a color change occurs, the reagent may be used to calculate the concentration of the aldehyde in the solution. Thus, after the solution is added to the reagent, the time for the color to reach a predetermined color standard is measured. This is then compared with a table of reaction times for that particular reagent and testing conditions (e.g., temperature) and the concentration of the aldehyde determined.

The reagent of the invention is particularly useful for the detection of formaldehyde and gluteraldehyde in rinse solutions of reusable medical equipment, such as hemodialyzers. It is not affected by saline concentrations up to 250 mEq/L or solutions containing dextrose at human serum concentrations. Other Schiff's reagents are useful only with pure water solutions of formaldehyde or gluteraldehyde under specific controlled conditions.

In a preferred embodiment, an accurately measured volume (e.g., 0.4 ml) of the reagent placed in a sealed glass ampule. The reagent is used by breaking off the top of the ampule, adding an accurately measured volume (e.g., 1.0 ml) of test solution (for instance, with a pipet or syringe), and determining whether a color change occurs.

The invention is further illustrated by the following Examples.

EXAMPLE 1

In a glass or plastic container, 300 g of sodium phosphate monobasic monohydrate is mixed into 600 ml of hot deionized water until dissolved. The solution is allowed to cool, and approximately 30 ml of orthophosphoric acid is added, with mixing overnight. The pH is carefully adjusted to 2.20±0.05 with additional orthophosphoric acid. Mixing is continued for one hour, the pH rechecked, and more orthophosphoric acid added if needed. If more acid is needed, the steps of mixing for one hour, rechecking the pH, and adding acid (if necessary) are repeated until the pH is correct and stable. In a second glass or plastic container, 0.40 g of para-rosanilin hydrochloride is combined with 150 ml of hot deionized water, and the solution is mixed for one hour. The solution is cooled, 2.0 g sodium metabisulfite is added, and the solution is mixed for one hour in a sealed container. This solution is then added to the first solution, with mixing. The total volume is then brought to 1.00 liter with deionized water. The solution is mixed and stored in a filled, sealed container. The reagent is particularly suited for detecting formaldehyde, and is evaluated by adding 0.2 ml of reagent to 1.0 ml of water containing various amounts of formaldehyde. The results are shown in Table I.

TABLE 1

| | | FORMALDEHYDE (mg/L) | | | |
|---|---|---|---|---|---|
| | | 1 | 2 | 5 | 10 |
| Time for Color | 23° C. | (a) | 10 | 2.5 | 1.5 |
| Change (Minutes)[b] | 37° C. | 5 | 2.25 | 1 | 0.5 |

[a] Did not reach the color.
[b] Time for solution to appear to be of the intensity of 10% red in the Murphy Color Guide Wheel.

EXAMPLE 2

The procedure of Example 1 is repeated with the following exceptions: the first solution is prepared with 400 g of sodium phosphate monobasic monohydrate and about 35 ml of orthophosphoric acid; the pH is adjusted to 2.70±0.05; and the second solution is prepared with 0.80 g of para-rosanilin hydrochloride. This reagent is particularly well suited for use in detecting gluteraldehyde.

I claim:

1. A method of preparing a modified Schiff's reagent comprising contacting together:
   (a) a para-rosaniline compound;
   (b) orthophosphoric acid;
   (c) a bisulfite compound;
   (d) a phosphate compound; and
   (e) water, in amounts such that a reagent having a pH within the range of 2.1 to 2.9 is formed that indicates by color change the presence of aldehyde in a water sample containing aldehyde at a concentration of 2 mg/L when mixed with such a water sample in a ratio of reagent to sample of from 1:1 to 1:10 on a volume basis.

2. The method of claim 1 wherein
   (i) the phosphate compound is added to the water to form a mixture, then
   (ii) the orthophosphoric acid is added to the mixture resulting from step (i), and then
   (iii) the para-rosaniline compound and the bisulfite compound are added to the mixture resulting from step (ii).

3. The method of claim 2 wherein after step (ii), the pH of the mixture resulting from step (ii) is 2.15 to 2.25.

4. A modified Schiff's reagent comprising:
   (a) a para-rosaniline compound;
   (b) orthophosphoric acid;
   (c) a bisulfite compound;
   (d) a phosphate compound; and
   (e) water, in amounts such that the reagent has a pH within the range of 2.1 to 2.9 and indicates by color change the presence of aldehyde in a water sample containing aldehyde at a concentration of 2 mg/L when mixed with such a water sample in a ratio of reagent to sample of from 1:1 to 1:10 on a volume basis.

5. The reagent of claim 4 wherein the para-rosaniline compound is present at 0.1 to 0.8 g/L, the orthophosphoric acid is present at 30 to 125 g/L, the bisulfite compound is present at 1 to 4 g/L, and the phosphate compound is present at 100 to 400 g/L.

6. The reagent of claim 5 wherein the para-rosaniline compound is present at 0.3 to 0.5 g/L, the orthophosphoric acid is present at 75 to 110 g/L, the bisulfite compound is present at 1.5 to 2.5 g/L, and the phosphate compound is present at 250 to 350 g/L.

7. The reagent of claim 6 wherein the para-rosaniline compound is present at 0.35 to 0.45 g/L, the orthophosphoric acid is present at 90 to 100 g/L, the bisulfite compound is present at 1.9 to 2.1 g/L, and the phosphate compound is present at 290 to 310 g/L.

8. The reagent of claim 4 or 5 wherein the para-rosaniline compound is para-rosaniline (free base), para-rosaniline hydrochloride, or para-rosanaline acetate.

9. The reagent of claim 8, wherein the para-rosaniline compound is para-rosaniline hydrochloride.

10. The reagent of claim 4 or 5 wherein the bisulfite compound is sodium metabisulfite, sodium bisulfite, potassium metabisulfite, or potassium bisulfite.

11. The reagent of claim 10, wherein the bisulfite compound is sodium metabisulfite.

12. The reagent of claim 4 or 5, wherein the phosphate compound is sodium or potassium orthophosphate monobasic, sodium or potassium orthophosphate dibasic, or sodium or potassium orthophosphate tribasic.

13. The reagent of claim 12, wherein the phosphate compound is sodium orthophosphate monobasic.

14. A method of detecting the presence of aldehyde in an aqueous solution comprising:
   (a) contacting an aqueous solution to be tested with the reagent of claim 5 to form a test mixture; and
   (b) determining whether a color change occurs in the test mixture, whereby any color change indicates the presence of aldehyde at a concentration of 2 mg/L or greater in the aqueous solution.

15. The method of claim 14 wherein the aqueous solution contains dextrose at human serum concentrations.

16. The method of claim 14 wherein the aqueous solution contains saline at a concentration not greater than 250 milliequivalents/L.

17. The method of claim 14 wherein the aldehyde comprises formaldehyde.

18. The method of claim 14 wherein the aldehyde comprises gluteraldehyde.

19. The method of claim 14 wherein the determination of whether a color change occurs takes place within 10 minutes of the contacting of step (a).

* * * * *